United States Patent

Gericke et al.

[11] Patent Number: 5,840,761
[45] Date of Patent: Nov. 24, 1998

[54] ALKYLBENZOYLGUANIDINE DERIVATIVES

[75] Inventors: Rolf Gericke, Seeheim-Jugenheim; Dieter Dorsch, Ober-Ramstadt; Manfred Baumgarth, Ober-Ramstadt; Klaus-Otto Minck, Ober-Ramstadt; Norbert Beier, Reinheim, all of Germany

[73] Assignee: Merck Patent Gesellschaft mit Beschrankter Haftung, Germany

[21] Appl. No.: 520,767

[22] Filed: Aug. 30, 1995

[30] Foreign Application Priority Data

Aug. 31, 1994 [DE] Germany ............. 4430916.3

[51] Int. Cl.⁶ ............. A61K 31/165; C07C 231/02; C07C 233/64
[52] U.S. Cl. ............. 514/617; 514/524; 514/618; 514/619; 514/620; 514/622; 558/411; 558/413; 558/415; 564/134; 564/138; 564/142; 564/162; 564/163; 564/170; 564/184
[58] Field of Search ............. 514/618, 619, 514/622, 617, 524, 620; 564/162, 163, 164, 170, 182, 183, 184, 134, 138, 142; 558/411, 413, 415

[56] References Cited

U.S. PATENT DOCUMENTS 5,571,842 11/1996 Kleemann et al. ............. 514/618

FOREIGN PATENT DOCUMENTS

| | | |
|---|---|---|
| 416499 | 3/1991 | European Pat. Off. . |
| 556672 | 2/1993 | European Pat. Off. . |
| 556673 | 2/1993 | European Pat. Off. . |
| 556674 | 2/1993 | European Pat. Off. . |
| 577024 | 6/1993 | European Pat. Off. . |
| 589336 | 9/1993 | European Pat. Off. . |
| 603650 | 12/1993 | European Pat. Off. . |
| 640588 | 8/1994 | European Pat. Off. . |

*Primary Examiner*—Shailendra Kumar
*Attorney, Agent, or Firm*—Millen, White, Zelano & Branigan, P.C.

[57] ABSTRACT

Alkylbenzoylguanidines of the formula I

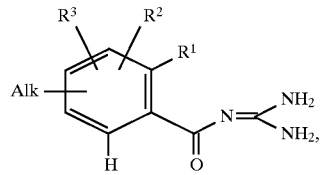

in which A, $R^1$, $R^2$ and $R^3$ have the given meanings, and their physiologically harmless salts exhibit antiarrhythmic properties and act as inhibitor of the cellular $Na^+/H^+$ antiporter.

17 Claims, No Drawings

ALKYLBENZOYLGUANIDINE DERIVATIVES

The invention relates to ortho-substituted alkylbenzoylguanidine derivatives of the formula I

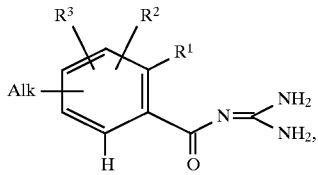

in which

R$^1$ is A, CF$_3$, CH$_2$F, CHF$_2$, C$_2$F$_5$, CN, NO$_2$, Hal, C≡CH or —X—R$^4$,

R$^2$ and R$^3$ are in each case, independently of each other, H, Hal, A, —X—R$^4$, CN, NO$_2$, CF$_3$, CH$_2$F, CHF$_2$, C$_2$F$_5$, CH$_2$CF$_3$, —SO$_n$—R$^6$, —SO$_2$NR$^4$R$^5$, Ph, OPh or Het, R$^4$ is H, A, cycloalkyl having from 5 to 7 C atoms, cycloalkylmethyl having from 6 to 8 C atoms, CF$_3$, CH$_2$F, CHF$_2$, CH$_2$CF$_3$, Ph or —CH$_2$—Ph, R$^5$ is H or A, or else R$^4$ and R$^5$ are together also alkylene having from 4 to 5 C atoms, where one CH$_2$ group can also be replaced by O, CO, S, >NH, >N—A or >N—CH$_2$—Ph R$^6$ is A or Ph, Alk is a straight-chain or branched C$_1$–C$_8$-alkyl radical, C$_3$–C$_8$-cycloalkyl which can be unsubstitued or substituted once, twice or three times by A, or is —CR$^7$=CHR$^{7'}$ or —C≡CR$^7$, R$^7$ and R$^{7'}$ are in each case, independently of each other, H, A, Ph or Het, Het is a mononuclear or binuclear, saturated, unsaturated or aromatic heterocycle having from 1 to 4 N, O and/or S atoms in the ring bonded via an N or C atom in the ring which can be unsubstituted or substituted once, twice or three times by Hal, CF$_3$, A, —X—R$^4$, CN, NO$_2$ and/or carbonyl oxygen A is alkyl having from 1 to 6 C atoms, Hal is F, Cl, Br or I, X is O, S or NR$^5$, Ph is phenyl which is unsubstituted or substituted once, twice or three times by A, OA, NR$^4$R$^5$, F, Cl, Br, I or CF$_3$, and n is 1 or 2, and the physiological tolerable salts thereof.

An object of the invention is to discover novel compounds having valuable properties, in particular those compounds which can be used for preparing medicaments.

Upon further study of the specification and appended claims, further objects and advantages of this invention will become apparent to those skilled in the art.

It was found that the compounds of the formula I, and their physiologically tolerable salts, possess valuable pharmacological properties while being well tolerated.

The novel compounds are inhibitors of the cellular Na$^+$/H$^+$ antiporter, i.e. active compounds which inhibit the cellular Na$^+$/H$^+$ exchange mechanism (Düsing et al., Med. Klin. 87, 378–384 (1992)), and thus provide good antiarrhythmic agents which are particularly suitable for treating arrhythmias which arise as a result of lack of oxygen.

The active compound of the acylguanidine group which is most well known is amiloride. However, this substance first and foremost exhibits hypotensive and saluretic effects, which are undesirable, when treating disturbances of cardiac rhythm, in particular, wherein the antiarrhythmic properties are only very weakly expressed.

In addition to this, EP 04 16 499, for example, discloses compounds which are structurally similar.

The invention relates to compounds of the formula I and to their physiologically harmless salts.

The novel substances of the present application exhibit a good cardioprotective effect and are therefore particularly suitable for the treatment of infarction, for infarction prophylaxis and for treating angina pectoris. In addition, the substances counteract all types of pathological hypoxic and ischaemic damage, so that the disorders which are caused primarily or secondarily by such damage can be treated. The active compounds are also well suited for preventive applications.

Because of the protective effects of these substances in pathological hypoxic or ischaemic situations, there are further possibilities for using these compounds in association with surgical interventions, for protecting organs which are from time to time less well supplied, in association with organ transplants, for protecting the organs which are being removed, in association with angioplastic blood vessel or cardiac surgery, in association with ischaemias of the nervous system, in association with the therapy of conditions of shock, and for prophylactic prevention of essential hypertension.

In addition, the compounds can also be employed as therapeutic agents in diseases arising from cell proliferation, such as arteriosclerosis, late complications in diabetes, tumor diseases, fibrotic diseases, in particular of the lung, liver and kidneys, and also organ hypertrophies and hyperplasias. In addition to this, the substances are also suitable for being used diagnostically for diagnosing diseases which are associated with an increased activity of the Na$^+$/H$^+$ antiporter, e.g. in erythrocytes, thrombocytes or leucocytes.

The effects of the compounds can be ascertained using methods which are known per se, as described, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Examples of suitable experimental animals are mice, rats, guinea pigs, dogs, cats, monkeys or pigs.

The compounds may, therefore, be used as pharmaceutically active compounds in human and veterinary medicine. In addition, they can be used as intermediates for preparing further pharmaceutically active compounds.

The compounds may be used as pharmaceutical agents in a manner analogous to ameloride and other known acylguanidine compounds, but exhibiting the advantages described herein, i.e., inhibition of the cellular Na$^+$/H+ exchange mechanism and activity in treatment of disturbances of cardiac rhythm. As intermediates, the compounds may be used to prepare pharmaceutically active compounds using synthetic methods analogous to those known in the art.

In the given formulae, A is a branched or unbranched alkyl group having 1–6, preferably 1–4, in particular 1, 2 or 3 C atoms, specifically methyl for preference, with ethyl, propyl, isopropyl, butyl or isobutyl also being preferred and sec-butyl, tert-butyl, pentyl, isopentyl (3-methylbutyl), hexyl or isohexyl (4-methylpentyl) furthermore being preferred.

R$^1$ is preferably A, OA (where X is 0 and R$^4$ is A) or Hal, in particular Br or Cl. However, it is also preferably CH$_2$F, CHF$_2$ CF$_3$ or C$_2$F$_5$.

R$^2$ and R$^3$ are preferably, independently of each other, H,—SO$_2$—A, A, CF$_3$, Cl, Br, CN or OA. Particularly preferably, one of the two radicals is —SO$_2$—CH$_3$, while the other has one of the previously mentioned preferred meanings br else is preferably hydrogen. One of the two radicals R$^2$ and R$^3$ is preferably located in the 3 or 5 position of the benzoyl group. If one of the radicals is —SO$_2$—A, it is then preferably located in the meta position with respect to the benzoylguanidine group.

R$^4$ is preferably H or A, as is R$^5$.

If R$^4$ and R$^5$ are together alkylene, the alkylene group is then preferably unbranched, specifically —(CH$_2$)$_k$— for preference, where k is 4 or 5; however —(CH$_2$)$_2$—O—CH$_2$)$_2$—, —(CH$_2$)$_2$—NH—(CH$_2$)$_2$—, —(CH$_2$)$_2$—NA—(CH$_2$)$_2$—, —CH$_2$—O—(CH$_2$)$_2$—, —CH$_2$—NH—(CH$_2$)$_2$—, or —CH$_2$—NA—(CH$_2$)$_2$— or —CO—(CH$_2$)$_3$—, —CO—(CH$_2$)$_4$— or —CH$_2$—CO—(CH$_2$)$_2$ are also preferred.

Ph is preferably phenyl which is unsubstituted or substituted once by Cl, Br, A, OA, NH$_2$, NHA, NA$_2$ or CF$_3$.

R$^6$ is preferably A, in particular methyl, or else, preferably, also unsubstituted phenyl.

The radical X is preferably O or NH.

Alk is preferably C$_1$ to C$_8$-alkyl or C$_3$ to C$_8$-cycloalkyl. If Alk is noncyclic, the radical is then, preferably, one of the alkyl radicals which are also preferred for A. Particularly preferred cycloalkyl radicals which can be Alk are cyclopropyl, cyclopentyl or cyclohexyl, or their derivatives which are substituted once by A, in particular methyl, ethyl or isopropyl.

R$^7$ and R$^{7'}$ are preferably, independently of each other, H, A or unsubstituted phenyl.

Hal is preferably F, Cl or Br.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl or 2-, 4-, 5-, 6-7- or 8-quinazolinyl. The heterocyclic radicals can also be partially or completely hydrogenated. Het can therefore also, for example, be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl or 1,2,3,4-tetrahydro-1-, -2-, -3-, -4-, -5-, -6-, -7- or -8-isoquinolinyl.

It applies generally that all the radicals, such as, for example, Het or Ph, which occur several times can be identical or different, i.e. are independent of each other.

Accordingly, the invention relates, in particular, to those compounds of the formula I in which at least one of the said radicals has one of the abovementioned, preferred meanings. Some preferred groups of compounds can be expressed by the following formulae Ia to Ih, which conform to the formula I and in which the radicals which are not more precisely described have the meaning given in association with formula I, in which, however, in Ia R$^1$ is A and R$^2$ is —SO$_2$—A or —SO$_2$—NH$_2$;

in Ib R$^1$ is A or Hal, and Alk is branched or unbranched alkyl having from 1 to 8 C atoms;

in Ic R$^1$ is A or Hal, and Alk is cycloalkyl having from 3 to 8 C atoms;

in Id Alk is located in the para position with respect to the asmide group, R$^2$ is —SO$_2$—A or —SO$_2$NH$_2$, and R$^1$ is A, OA or Hal;

in Ie Alk is located in the para position with respect to the amide group and is methyl, ethyl, propyl or isopropyl, and R$^2$ is located in the meta position with respect to the amide group and is —SO$_2$—A;

in If R$^1$ and R$^2$ are adjacent to each other and R$^1$ is A, OA or Hal, and R$^2$ is —SO$_2$—A;

in Ig Alk is located in the para position with respect to the amide group and is cyclopropyl, cyclopentyl or cyclohexyl, and R$^2$ is located in the meta position with respect to the amide group and is —SO$_2$—A;

in Ih R$^1$ is A, OA or Hal, R$^2$ is SO$_2$—A, and Alk is methyl, ethyl, propyl, isopropyl, cyclopentyl or cyclohexyl.

The invention also relates to a process for preparing the compounds of the formula I and also the salt thereof, characterized in that a compound of the formula II

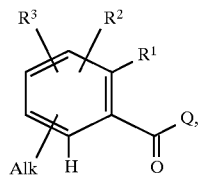

in which R$^1$, R$^2$, R$^3$ and Alk have the previously mentioned meanings, and Q is Cl, Br, OA, O—CO—A, O—CO—Ph, OH, or another reactive esterified OH group or a leaving group which can readily be substituted nucleophilically, is reacted with guanidine, or in that a benzoylguanidine of the formula III

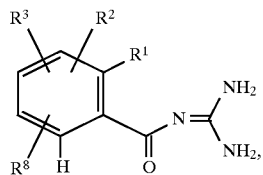

in which R$^1$, R$^2$ and R$^3$ have the previously mentioned meanings, and

R$^8$ is F, Cl, Br, I or H, is reacted with a compound of the formula IV

in which

Alk has the given meaning, and

R$^{8'}$ is H, Cl, Br or I, in the presence of a catalyst and following prior metalation or transmetalation, or in that a compound which contains one or more reducible group(s) and/or one or more additional C—C and/or C—N bond(s) in place of one or more hydrogen atoms, but which otherwise conforms to the formula I, is treated with a reducing agent, or in that a compound which contains one or more solvolysable group(s) in place of one or more hydrogen atoms, but which otherwise conforms to the formula I, is treated with a solvolysing agent, and/or in that a base of the formula I which has been obtained is converted into one of its salts by being treated with an acid.

The compounds of the formula I are otherwise prepared by methods which are known per se, as described in the literature (e.g. in the standard works such as Houben-Weyl, Methoden der organischen Chemie (Methods of organic chemistry), Georg-Thieme-Verlag, Stuttgart; Organic Reactions, John Wiley & Sons, Inc., New York; and also in the abovementioned patent application), and specifically under reaction conditions which are known for the said reactions and which are suitable for these reactions. In this context, use can also be made of variants which are known per se but which have not been mentioned in any detail here.

If desired, the starting compounds may also be formed in situ, such that they are not isolated from the reaction mixture but are instead immediately subjected to further reaction to form the compounds of the formula I.

Preferably, compounds of the formula I are prepared by reacting an activated carboxylic acid derivative of the formula II, where Q is particularly preferably Cl or —O—CH$_3$, with guanidine. Reaction variants are also particularly suitable in which the free carboxylic acid (formula II where Q=OH) is converted, in a manner known per se, into the particular activated derivative and this latter derivative is then directly, without intermediate isolation, reacted with guanidine. Examples of methods in which intermediate isolation can be dispensed with are activation with carbonyldiimidazole or dicyclohexylcarbodiimide or the Mukayama,variant (Angew. Chem. 91, 788–812 (1979)).

Generally, the carboxylic acids and carboxylic acid derivatives of the formula II are known. They are prepared, in particular, by Pd-catalyzed cross-couplings. Examples of preferred catalysts are Pd(PPh$_3$)$_4$, (Ph$_3$P)$_2$PdCl$_2$, Pd(CH$_3$COO)$_2$ or Pd(II) 1,1'-bis(diphenylphosphine) ferrocene chloride, preferably in the presence of CuI.

The carboxylic acids of the formula II, or their derivatives, are furthermore prepared by metalating suitable benzoic acid derivatives of the formula V

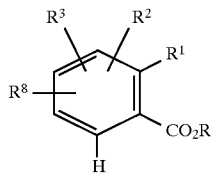

V in which R$^1$, R$^2$, R$^3$ and R$^8$ have the given meanings, and R is H or A, and then reacting them with an alkyl halide of the formula IV. An example of a suitable base for the metalation is lithium diisopropylamide.

In the previously mentioned cross-couplings, a carboxylic acid derivative or an ester derivative of the formula V, in which R$^8$ is Cl, Br or I, is reacted with an organometallic alkyl compound, which is prepared in situ from a compound of the formula IV by metalating with a metalating reagent which is known per se, in the presence of a suitable metal catalyst, in particular one of those which have previously been mentioned.

The reaction is carried out in analogy with the reaction of the compounds III and IV. It is described below.

The reaction of a reactive carboxylic acid derivative of the formula II with guanidine is effected in a manner known per se, preferably in a protic or aprotic, polar or non-polar, inert organic solvent.

Suitable solvents for the reaction of the compounds III and IV are mentioned below. However, particularly preferred solvents are methanol, THF, dimethoxyethane, dioxane or mixtures prepared therefrom, and also water. Temperatures of from about 20° C. to the boiling point of the solvent for example are suitable as the reaction temperature. The reaction times are preferably about 5 min to 12 hrs. It is expedient to include an acid-capturing agent in the reaction. Any type of base which does not interfere with the reaction itself is suitable for this purpose. However, the use of inorganic bases, such as potassium carbonate, or of organic bases, such as triethylamine or pyridine, or else an excess of the guanidine, is particularly suitable.

Compounds of the formula I according to claim 1 can also be prepared by reacting a benzoylguanidine of the formula III with a compound of the formula IV. The starting compounds of the formula III can be prepared, in a simple manner, by reacting appropriately substituted benzoic acids, or reactive acid derivatives, such as, for example, acid halides, esters or anhydrides, which can be derived therefrom, with guanidine under reaction conditions which are known per se for amide preparation and which are generally customary. Those reaction variants are once again particularly suitable which were previously specified for the reaction of compound II with guanidine.

The compounds of the formula IV, like the methods for their preparation, are known per se. If they are not known, they can be prepared by methods which are known per se.

Preparation of the compound II, and also reaction of the compound III with a compound of the formula IV, are effected in a manner known per se, preferably in a protic or aprotic polar, inert organic solvent.

In the preparation of II, or in the reaction of III with IV, it is likewise expedient to carry out the reaction in the presence of a base or with an excess of the basic component. Preferred examples of suitable bases are alkali metal or alkaline earth metal hydroxides, carbonates or alcoholates, or organic bases such as triethylamine or pyridine, which can also be used in excess and which can then simultaneously serve as solvent.

Suitable inert solvents are, in particular, alcohols, such as methanol, ethanol, isopropanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methyl glycol or ethyl glycol) or ethylene glycol dimethyl ether (diglyme); ketones, such as acetone or butanone; nitriles, such as acetonitrile; nitro compounds, such as nitromethane or nitrobenzene; esters, such as ethyl acetate; amides such as hexamethylphosphoric triamide; sulfoxides, such as dimethyl sulfoxide (DMSO); chlorinated hydrocarbons, such as dichloromethane, chloroform, trichloroethylene, 1,2-dichloroethane or carbon tetrachloride; hydrocarbons, such as benzene, toluene or xylene. In addition to this, mixtures of these solvents with each other are also suitable.

A particularly preferred procedure in the reaction of III with IV consists in suspending the corresponding benzoylguanidine in an inert solvent, such as, for example, toluene, treating it with a Pd(II) catalyst, and then adding dropwise the desired, previously transmetalated, compound, for example a Zn alkyl compound, of the formula IV.

The compounds of the formula I can also be obtained by releasing them from their functional derivatives by means of solvolysis, in particular hydrolysis, or by means of hydrogenolysis.

Starting compounds preferred for the solvolysis or hydrogenolysis are those which contain, in place of one or more free amino groups and/or hydroxyl groups, corresponding, protected amino groups and/or hydroxyl groups, but which otherwise conform to the formula I, preferably those starting compounds which carry an amino protective group in place of a H atom which is bonded to a N atom, in particular those starting compounds which carry an R'—N group, in which R' is an amino protective group, in place of a HN group, and/or those starting compounds which carry a hydroxyl protective. group in place of the H atom of a hydroxyl group, for example those starting compounds which carry an OR" group, in which R" is a hydroxyl protective group, in place of an OH group, but which otherwise conform to the formula I.

Several—identical or different—protected amino groups and/or hydroxyl groups may be present in the molecule of the starting compound. If the protective groups which are present differ from each other, they can in many cases be eliminated selectively.

The expression "amino protective group" is well known and refers to groups which are suitable for protecting (for blocking) an amino group against chemical reactions but which can readily be removed once the desired chemical reaction has been carried out at another site in the molecule. Typical examples of such groups are, in particular, unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl or triphenylmethyl). Since the amino protective groups are removed after the end of the desired reaction (or sequence of reactions), their nature and size is otherwise not critical; nevertheless, those are preferred which have 1–20, in particular 1–8, C atoms. In connection with the present process, the expression "acyl group" is to be interpreted in the widest possible sense. It encompasses acyl groups which are derived from aliphatic, araliphatic, aromatic or heterocyclic carboxylic acids or sulfonic acids, and also, in particular, alkoxy carbonyl groups, aryloxycarbonyl groups and, especially, aralkoxycarbonyl groups. Examples of acyl groups of this nature are alkanoyl, such as acetyl, propionyl or butyryl; aralkanoyl, such as phenylacetyl; aroyl, such as benzoyl or toluyl; aryloxyalkanoyl, such as phenoxyacetyl; alkoxycarbonyl, such as methoxycarbonyl, ethoxycarbonyl, 2,2,2-trichloroethoxycarbonyl, isopropoxycarbonyl, tert-butoxycarbonyl (BOC) or 2-iodoethoxycarbonyl; aralkyloxycarbonyl, such as benzyloxycarbonyl (CBZ), 4-methoxybenzyloxycarbonyl or 9-fluorenylmethoxycarbonyl (FMOC). Amino protective groups which are preferred are BOC, DNP and BOM, and also CBZ, benzyl and acetyl.

The expression "hydroxyl protective group" is likewise well known and refers to groups which are suitable for protecting a hydroxyl group against chemical reactions, but which are readily removed once the desired chemical reaction has been carried out at another site in the molecule. Typical examples of such groups are the abovementioned unsubstituted or substituted aryl, aralkyl or acyl groups, and also alkyl groups. The nature and the size of the hydroxyl protective groups is not critical, since they are removed once again after the end of the desired chemical reaction or sequence of reactions; groups having 1–20, in particular 1–10, C atoms are preferred. Examples of hydroxyl protective groups are, inter alia, tert-butyl, benzyl, p-nitrobenzoyl, p-toluene sulfonyl and acetyl, with benzyl and acetyl being particularly preferred.

The functional derivatives of the compounds of the formula I which are to be used as starting compounds may be prepared by customary methods, as described, for example, in the specified standard works and patent applications, for example by the reaction of compounds which conform to the formulae II and III, with, however, at least one of these compounds containing a protective group in place of a H atom.

Depending on the protective group employed, liberation of the compounds of the formula I from their functional derivatives is achieved, for example, using strong acids, expediently using trifluoroacetic acid or perchloric acid, or else using other strong inorganic acids such as hydrochloric acid or sulfuric acid, or strong organic carboxylic acids such as trichloroacetic acid, or sulfonic acids such as benzene sulfonic acid or p-toluene sulfonic acid. It is possible, but not always necessary, for an additional inert solvent to be present.

Suitable inert solvents are preferably organic, for example carboxylic acids, such as acetic acid, ethers, such as tetrahydrofuran (THF) or dioxane, amides, such as dimethylformamide (DMF), halogenated hydrocarbons, such as dichloromethane, and also alcohols, such as methanol, ethanol or isopropanol, and also water. Mixtures of the previously mentioned solvents are also suitable. Trifluoroacetic acid is preferably used in excess without the addition of any further solvent; perchloric acid is preferably used in the form of a mixture consisting of acetic acid and 70% perchloric acid in a ratio of 9:1. The reaction temperatures for the cleavage are expediently from about 0 to about 50° C.; the reaction is preferably carried out at 15°–30° C. (room temperature).

The BOC group can, for example, preferably be eliminated using 40% trifluoroacetic acid in dichloromethane or using from about 3 to 5N HCl in dioxane at 15°–60°, while the FMOC group can be eliminated using an approximately 5–20% solution of dimethylamine, diethylamine or piperidine in DMF at 15°–50°. Elimination of the DNP group is also achieved, for example, using an approximately 3–10% solution of 2-mercaptoethanol in DMF/water at 15°–30°.

Protective groups (e.g. BOM, CBZ or benzyl) which can be removed hydrogenolytically can be eliminated, for example, by treatment with hydrogen in the presence of a catalyst (e.g. of a precious metal catalyst such as palladium, expediently on a support such as carbon). The abovementioned solvents are suitable in this context, in particular, for example, alcohols, such as methanol or ethanol, or amides, such as DMF. As a rule, the hydrogenolysis is carried out at temperatures of from about 0°–100° C. and under pressures of from about 1 to 200 bar, preferably at 20°–30° C. and under 1–10 bar. Successful hydrogenolysis of the CBZ group is achieved, for example, on 5–10% Pd-C in methanol at 20°–30° C.

A base of the formula I can also be converted into the affiliated acid addition salt using an acid. Acids which are suitable for this reaction are those which give rise to physiologically harmless salts. Thus, use can be made of inorganic acids, for example sulfuric acid, nitric acid, hydrohalic acids, such as hydrochloric acid or hydrobromic acid, phosphoric acids, such as orthophosphoric acid, or sulfamic acid, and also of organic acids, in particular aliphatic, alicyclic, araliphatic, aromatic or heterocyclic monobasic or polybasic carboxylic acids, sulfonic acids or sulfuric acids, e.g. formic acid, acetic acid, propionic acid, pivalic acid, diethylacetic acid, malonic acid, succinic acid, pimelic acid, filmaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalene monosulfonic and disulfonic acids or laurylsulfuric acid.

The compounds of the formula I and their physiologically harmless salts may be used to produce pharmaceutical preparations, especially by a non-chemical route. When being used for this purpose, they can be brought, together with at least one solid, liquid and/or semiliquid carrier substance or auxiliary substance and, where appropriate, in combination with one or more additional active compound (s), into a suitable dosage form.

The invention furthermore relates to compositions, in particular pharmaceutical preparations, which contain at least one compound of the formula I and/or one of its physiologically harmless salts.

These preparations can be used as medicaments in human or veterinary medicine. Suitable carrier substances are organic or inorganic substances which are suitable for enteral (e.g. oral), parenteral or topical administration and which do not react with the novel compounds, for example water, vegetable oils, benzyl alcohols, polyethylene glycols, glycerol triacetate, gelatin, carbohydrates, such as lactose or starch, magnesium stearate, talc, lanolin or vaseline. For oral application, use is made, in particular, of tablets, coated tablets, capsules, syrups, juices or drops, for rectal application of suppositories, for parenteral application of solutions, preferably oily or aqueous solutions, and also of suspensions, emulsions or implants, and for topical application of ointments, creams, pastes, lotions, gels, sprays, foams, aerosols, solutions. (e.g. solutions in alcohols, such as ethanol or isopropanol, acetonitrile, DMF, dimethylacetamide or 1,2-propanediol, or their mixtures with each other and/or with water) or powders. The novel compounds can also be lyophilized and the resulting lyophilizates used, for example, to produce preparations for injection.

Liposomal preparations are also especially suitable for topical application. The given preparations can be sterilized and/or contain auxiliary substances such as glidants, preservatives, stabilizers and/or wetting agents, emulsifiers, salts for influencing the osmotic pressure, buffering substances, coloring substances, flavoring substances and/or aromatizing substances. They can, if desired, also contain one or more additional active compounds, e.g. one or more vitamins.

The compounds of the formula I, and their physiologically harmless salts, can be administered to humans or animals, in particular mammals such as monkeys, dogs, cats, rats or mice, and be used for the therapeutic treatment of the human or animal body and also for controlling diseases, in particular in association with the therapy and/or prophylaxis of disturbances of the cardiovascular system. They are suitable, therefore, for treating arrhythmias, in particular when the latter are caused by a lack of oxygen, angina pectoris, infarctions, ischaemias of the nervous system, such as, for example, stroke or cerebral oedemas, and conditions of shock, and also for preventive treatment.

The substances can also be employed as therapeutic agents in diseases in which cell proliferation plays a role, such as arteriosclerosis, late complications in diabetes, tumor diseases, fibroses and organ hypertrophies and hyperplasias, in particular diseases of the prostate.

In this context, the substances according to the invention may be administered in analogy with known antiarrhythmics e.g. apridine, preferably in doses of from about 0.01–5 mg, in particular of from 0.02–0.5 mg per dosage unit. The daily dose is preferably from about 0.0001–0.1, in particular from 0.0003–0.01, mg/kg of body weight. However, the special dose for each particular patient depends on a wide variety of factors, for example on the activity of the special compound employed, on the age, on the body weight, on the general state of health, on the sex, on the diet, on the time and route of administration, on the speed of excretion, on the combination of medicines being employed, and on the severity of the particular disease to which the therapy applies. Oral administration is preferred.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. P 44 30 916.3, filed Aug. 31, 1994, is hereby incorporated by reference.

In the examples which follow, "customary working-up" denotes:

If required, water is added and extraction takes place using an organic solvent such as ethyl acetate; the organic phase is separated off and dried over sodium sulfate, after which it is filtered and evaporated; the residue is purified by chromatography and/or crystallization.

EXAMPLE 1

A solution of 1.4 g of methyl 2-methyl-4-isopropyl-5-methylsulfonylbenzoate [obtainable by reacting methyl 2-methyl-4-bromo-5-methylsulfonylbenzoate with isopropylzinc chloride in the presence of Pd(II) 1,1'-bis (diphenylphosphine)ferrocene chloride and CuI] and 1.5 g of guanidine in 50 ml of methanol is boiled for five hours and the solvent is then removed. The residue is treated with water and the remaining crystalline crop is filtered off with suction and treated with dil. sodium hydroxide solution. The solid residue is filtered off and recrystallized from ethanol, and N-diaminomethylene-2-methyl-4-isopropyl-5-methylsulfonylbenzamide is obtained, m.p. 220°–223°.

The following are obtained in an analogous manner by reacting guanidine
with methyl 2,4-dimethyl-5-methylsulfonylbenzoate,
  N-diaminomethylene-2,4-dimethyl-5-methylsulfonylbenzamide m.p. 197°;
with methyl 2-methyl-4-ethyl-5-methylsulfonylbenzoate,
  N-diaminomethylene-2-methyl-4-ethyl-5-methylsulfonylbenzamide, m.p. 197°–198°; m.p. 235°–236° (methansulfonate);
with methyl 2-methyl-4-propyl-5-methylsulfonylbenzoate,
  N-diaminomethylene-2-methyl-4-propyl-5-methylsulfonylbenzamide;
with methyl 2-methyl-4-butyl-5-methylsulfonylbenzoate,
  N-diaminomethylene-2-methyl-4-butyl-5-methylsulfonylbenzamide;
with methyl 2-methyl-4-(2-butyl)-5-methylsulfonylbenzoate, N-diaminomethylene-2-methyl-4-(2-butyl)-5-methylsulfonylbenzamide;
with methyl 2-methyl-4-pentyl-5-methylsulfonylbenzoate,
  N-diaminomethylene-2-methyl-4-pentyl-5-methylsulfonylbenzamide;

with methyl 2-methyl-4-(2-pentyl)-5-methylsulfonylbenzoate, N-diaminomethylene-2-methyl-4-(2-pentyl)-5-methylsulfonylbenzamide;
with methyl 2-methyl-4-(3-pentyl)-5-methylsulfonylbenzoate, N-diaminomethylene-2-methyl-4-(3-pentyl)-5-methylsulfonylbenzamide;
with methyl 2-methyl-4-hexyl-5-methylsulfonylbenzoate, N-diaminomethylene-2-methyl-4-hexyl-5-methylsulfonylbenzamide;
with methyl 2-methyl-4-(2-hexyl)-5-methylsulfonybenzoate, N-diaminomethylene-2-methyl-4-(2-hexyl)-5-methylsulfonylbenzamide;
with methyl 2-methyl-4-cyclobutyl-5-methylsulfonylbenzoate, N-diaminomethylene-2-methyl-4-cyclobutyl-5-methylsulfonylbenzamide;
with methyl 2-methyl-4-cyclopropyl-5-methylsulfonylbenzoate, N-diaminomethylene-2-methyl-4-cyclopropyl-5-methylsulfonylbenzamide;
with methyl 2-methyl-4-cyclopentyl-5-methylsulfonylbenzoate, N-diaminomethylene-2-methyl-4-cyclopentyl-5-methylsulfonylbenzamide, m.p. 120°–125°; m.p. 199°–200° (methanesulfonate);
with methyl 2-methyl-4-cyclohexyl-5-methylsulfonylbenzoate, N-diaminomethylene-2-methyl-4-cyclohexyl-5-methylsulfonylbenzamide;
with methyl 2-methyl-4-isobutyl-5-methylsulfonylbenzoate, N-diaminomethylene-2-methyl-4-isobutyl-5-mathylsulfonylbenzamide;
with methyl 2-methyl-4-tert-butyl-5-methylsulfonylbenzoate, N-diaminomethylene-2-methyl-4-tert.-butyl-5-methylsulfonylbenzamide;
with methyl 2,4-diethyl-5-methylsulfonylbenzoate, N-diaminomethylene-2,4-diethyl-5-methylsulfonylbenzamide;
with methyl 2-ethyl-4-methyl-5-methylsulfonylbenzoate, N-diaminomethylene-2-ethyl-4-methyl-5-methylsulfonylbenzamide;
with methyl 2-ethyl-4-isopropyl-5-methylsulfonylbenzoate, N-diaminomethylene-2-ethyl-4-isopropyl-5-methylsulfonylbenzamide;
with methyl 2-ethyl-4-propyl-5-methylsulfonylbenzoate, N-diaminomethylene-2-ethyl-4-propyl-5-methylsulfonylbenzamide;
with methyl 2-ethyl-4-butyl-5-methylsulfonylbenzoate, N-diaminomethylene-2-ethyl-4-butyl-5-methylsulfonylbenzamide;
with methyl 2-ethyl-4-(2-butyl)-5-methylsulfonylbenzoate, N-diaminomethylene-2-ethyl-4-(2-butyl)-5-methylsulfonylbenzamide;
with methyl 2-ethyl-4-pentyl-5-methylsulfonylbenzoate, N-diaminomethylene-2-ethyl-4-pentyl-5-methylsulfonylbenzamide;
with methyl 2-ethyl-4-(2-pentyl)-5-methylsulfonylbenzoate, N-diaminomethylene-2-ethyl-4-(2-pentyl)-5-methylsulfonylbenzamide;
with methyl 2-ethyl-4-(3-pentyl)-5-methylsulfonylbenzoate, N-diaminomethylene-2-ethyl-4-(3-pentyl)-5-methylsulfonylbenzamide;
with methyl 2-ethyl-4-hexyl-5-methylsulfonylbenzoate, N-diaminomethylene-2-ethyl-4-hexyl-5-methylsulfonylbenzamide;
with methyl 2-ethyl-4-(2-hexyl)-5-methylsulfonylbenzoate, N-diaminomethylene-2-ethyl-4-(2-hexyl)-5-methylsulfonylbenzamide;
with methyl 2-ethyl-4-(3-hexyl)-5-methylsulfonylbenzoate, N-diaminomethylene-2-ethyl-4-(3-hexyl)-5-methylsulfonylbenzamide;
with methyl 2-ethyl-4-cyclopropyl-5-methylsulfonylbenzoate, N-diaminomethylene-2-ethyl-4-cyclopropyl-5-methylsulfonylbenzamide;
with methyl 2-ethyl-4-cyclopentyl-5-methylsulfonylbenzoate, N-diaminomethylene-2-ethyl-4-cyclopentyl-5-methylsulfonylbenzamide;
with methyl 2-ethyl-4-cyclohexyl-5-methylsulfonylbenzoate, N-diaminomethylene-2-ethyl-4-cyclohexyl-5-methylsulfonylbenzamide;
with methyl 2-ethyl-4-(2-methylcyclopentyl)-5-methylsulfonybenzoate, N-diaminomethylene-2-ethyl-4-(2-methylcyclopentyl)-5-methylsulfonylbenzamide;
with methyl 2-ethyl-4-(4-methylcyclohexyl)-5-methylsulfonylbenzoate, N-diaminomethylene-2-ethyl-4-(4-methylcyclohexyl)-5-methylsulfonylbenzamide;
with methyl 2,4-dipropyl-5-methylsulfonylbenzoate, N-diaminomethylene-2,4-dipropyl-5-methylsulfonylbenzamide;
with methyl 2-propyl-4-methyl-5-methylsulfonylbenzoate, N-diaminomethylene-2-propyl-4-methyl-5-methylsulfonylbenzamide;
with methyl 2-propyl-4-isopropyl-5-methylsulfonylbenzoate, N-diaminomethylene-2-propyl-4-isopropyl-5-methylsulfonylbenzamide;
with methyl 2-propyl-4-ethyl-5-methylsulfonylbenzoate, N-diaminomethylene-2-propyl-4-ethyl-5-methylsulfonylbenzamide;
with methyl 2-propyl-4-butyl-5-methylsulfonylbenzoate, N-diaminomethylene-2-propyl-4-butyl-5-methylsulfonylbenzamide;
with methyl 2-propyl-4-(2-butyl)-5-methylsulfonylbenzoate, N-diaminomethylene-2-propyl-4-(2-butyl)-5-methylsulfonylbenzamide;
with methyl 2-propyl-4-pentyl-5-methylsulfonylbenzoate, N-diaminomethylene-2-propyl-4-pentyl-5-methylsulfonylbenzamide;
with methyl 2-propyl-4-(2-pentyl)-5-methylsulfonylbenzoate, N-diaminomethylene-2-propyl-4-(2-pentyl)-5-methylsulfonylbenzamide;
with methyl 2-propyl-4-(3-pentyl)-5-methylsulfonylbenzoate, N-diaminomethylene-2-propyl-4-(3-pentyl)-5-methylsulfonylbenzamide;
with methyl 2-propyl-4-hexyl-5-methylsulfonylbenzoate, N-diaminomethylene-2-propyl-4-hexyl-5-methylsulfonylbenzanide;
with methyl 2-propyl-4-(2-hexyl)-5-methylsulfonylbenzoate, N-diaminomethylene-2-propyl-4-(2-hexyl)-5-methylsulfonylbenzamide;
with methyl 2-propyl-4-(3-hexyl)-5-methylsulfonylbenzoate, N-diaminomethylene-2-propyl-4-(3-hexyl)-5-methylsulfonylbenzamide;
with methyl 2-propyl-4-cyclopropyl-5-methylsulfonylbenzoate, N-diaminomethylene-2-propyl-4-cyclopropyl-5-methylsulfonylbenzamide;
with methyl 2-propyl-4-cyclopentyl-5-methylsulfonylbenzoate, N-diaminomethylene-2-propyl-4-cyclopentyl-5-methylsulfonylbenzamide;
with methyl 2-propyl-4-cyclohexyl-5-methylsulfonylbenzoate, N-diaminomethylene-2-propyl-4-cyclohexyl-5-methylsulfonylbenzamide;
with methyl 2-propyl-4-(2-methylcyclopentyl)-5-methylsulfonylbenzoate, N-diaminomethylene-2-propyl-4-(2-methylcyclopentyl)-5-methylsulfonylbenzamide;
with methyl 2-propyl-4-(4-methylcyclohexyl)-5-methylsulfonylbenzoate, N-diaminomethylene-2-propyl-4-(4-methylcyclohexyl)-5-methylsulfonylbenzamide.

EXAMPLE 2

In analogy with Example 1, N-diaminomethylene-2-bromo-4-methyl-5-methylsulfonylbenzamide is obtained by reacting 1.8 g of methyl 2-bromo-4-methyl-5-methylsulfonylbenzoate [obtainable by reacting methyl 2,4-dibromo-5-methylsulfonylbenzoate with methylzinc chloride] with 1.5 g of guanidine in methanol.

The following are obtained in an analogous manner by reacting guanidine with methyl 2-fluoromethyl-4-methyl-5-methylsulfonylbenzoate, N-diaminomethylene-2-fluoromethyl-4-dimethyl-5-methylsulfonylbenzamide;

with methyl 2-difluoromethyl-4-ethyl-5-methylsulfonylbenzoate, N-diaminomethylene-2-difluoromethyl-4-ethyl-5-methylsulfonylbenzamide;

with methyl 2-bromo-4-propyl-5-methylsulfonylbenzoate, N-diaminomethylene-2-bromo-4-propyl-5-methylsulfonylbenzamide;

with methyl 2-chloro-4-butyl-5-methylsulfonylbenzoate, N-diaminomethylene-2-chloro-4-butyl-5-methylsulfonylbenzamide;

with methyl 2-bromo-4-(2-butyl)-5-methylsulfonylbenzoate, N-diaminomethylene-2-bromo-4-(2-butyl)-5-methylsulfonylbenzamide;

with methyl 2-trifluoromethyl-4-pentyl-5-methylsulfonylbenzoate, N-diaminomethylene-2-trifluoromethyl-4-pentyl-5-methylsulfonylbenzamide;

with methyl 2-fluoromethyl-4-(2-pentyl)-5-methylsulfonylbenzoate, N-diaminomethylene-2-fluoromethyl-4-(2-pentyl)-5-methylsulfonylbenzamide;

with methyl 2-bromo-4-(3-pentyl)-5-methylsulfonylbenzoate, N-diaminomethylene-2-bromo-4-(3-pentyl)-5-methylsulfonylbenzamide;

with methyl 2-chloro-4-hexyl-5-methylsulfonylbenzoate, N-diaminomethylene-2-chloro-4-hexyl-5-methylsulfonylbenzamide;

with methyl 2-difluoromethyl-4-(2-hexyl)-5-methylsulfonylbenzoate, N-diaminomethylene-2-difluoromethyl-4-(2-hexyl)-5-methylsulfonylbenzamide;

with methyl 2-bromo-4-(3-hexyl)-5-methylsulfonylbenzoate, N-diaminomethylene-2-bromo-4-(3-hexyl)-5-methylsulfonylbenzamide;

with methyl 2-bromo-4-cyclopropyl-5-methylsulfonylbenzoate, N-diaminomethylene-2-bromo-4-cyclopropyl-5-methylsulfonylbenzamide;

with methyl 2-bromo-4-cyclopentyl-5-methylsulfonylbenzoate, N-diaminomethylene-2-bromo-4-cyclopentyl-5-methylsulfonylbenzamide;

with methyl 2-bromo-4-cyclohexyl-5-methylsulfonylbenzoate, N-diaminomethylene-2-bromo-4-cyclohexyl-5-methylsulfonylbenzamide;

with methyl 2-bromo-4-(2-methylcyclopentyl)-5-methylsulfonylbenzoate, N-diaminomethylene-2-bromo-4-(2-methylcyclopentyl)-5-methylsulfonylbenzamide;

with methyl 2-bromo-4-(4-methylcyclohexyl)-5-methylsulfonylbenzoate, N-diaminomethylene-2-bromo-4-(4-methylcyclohexyl)-5-methylsulfonylbenzamide;

with methyl 2-cyano-4-ethyl-5-methylsulfonylbenzoate, N-diaminomethylene-2-cyano-4-ethyl-5-methylsulfonylbenzamide;

with methyl 2-cyano-4-methyl-5-methylsulfonylbenzoate, N-diaminomethylene-2-cyano-4-methyl-5-methylsulfonylbenzamide;

with methyl 2-cyano-4-isopropyl-5-methylsulfonylbenzoate, N-diaminomethylene-2-cyano-4-isopropyl-5-methylsulfonylbenzamide;

with methyl 2-cyano-4-propyl-5-methylsulfonylbenzoate, N-diaminomethylene-2-cyano-4-propyl-5-methylsulfonylbenzamide;

with methyl 2-nitro-4-butyl-5-methylsulfonylbenzoate, N-diaminomethylene-2-nitro-4-butyl-5-methylsulfonylbenzamide;

with methyl 2-ethynyl-4-(2-butyl)-5-methylsulfonylbenzoate, N-diaminomethylene-2-ethynyl-4-(2-butyl)-5-methylsulfonylbenzamide;

with methyl 2-ethynyl-4-pentyl-5-methylsulfonylbenzoate, N-diaminomethylene-2-ethynyl-4-pentyl-5-methylsulfonylbenzamide;

with methyl 2-cyano-4-(2-pentyl)-5-methylsulfonylbenzoate, N-diaminomethylene-2-cyano-4-(2-pentyl)-5-methylsulfonylbenzamide;

with methyl 2-nitro-4-(3-pentyl)-5-methylsulfonylbenzoate, N-diaminomethylene-2-nitro-4-(3-pentyl)-5-methylsulfonylbenzamide;

with methyl 2-ethynyl-4-hexyl-5-methylsulfonylbenzoate, N-diaminomethylene-2-ethynyl-4-hexyl-5-methylsulfonylbenzamide;

with methyl 2-cyano-4-(2-hexyl)-5-methylsulfonylbenzoate, N-diaminomethylene-2-cyano-4-(2-hexyl)-5-methylsulfonylbenzamide;

with methyl 2-pentafluoroethyl-4-(3-hexyl)-5-methylsulfonylbenzoate, N-diaminomethylene-2-pentafluoroethyl-4-(3-hexyl)-5-methylsulfonylbenzamide;

with methyl 2-cyano-4-cyclopropyl-5-methylsulfonylbenzoate, N-diaminomethylene-2-cyano-4-cyclopropyl-5-methylsulfonylbenzamide;

with methyl 2-ethynyl-4-cyclopentyl-5-methylsulfonylbenzoate, N-diaminomethylene-2-ethynyl-4-cyclopentyl-5-methylsulfonylbenzamide;

with methyl 2-cyano-4-cyclohexyl-5-methylsulfonylbenzoate, N-diaminomethylene-2-cyano-4-cyclohexyl-5-methylsulfonylbenzamide;

with methyl 2-nitro-4-(2-methylcyclopentyl)-5-methylsulfonylbenzoate, N-diaminomethylene-2-nitro-4-(2-methylcyclopentyl)-5-methylsulfonylbenzamide;

with methyl 2-pentafluoroethyl-4-(4-methylcyclohexyl)-5-methylsulfonylbenzoate, N-diaminomethylene-2-pentafluoroethyl-4-(4-methylcyclohexyl)-5-methylsulfonylbenzamide;

with methyl 2-pentafluoroethyl-4-propyl-5-methylsulfonylbenzoate, N-diaminomethylene-2-pentafluoroethyl-4-propyl-5-methylsulfonylbenzamide;

with methyl 2-methoxy-4-methyl-5-methylsulfonylbenzoate, N-diaminomethylene-2-methoxy-4-methyl-5-methylsulfonylbenzamide;

with methyl 2-methoxy-4-isopropyl-5-methylsulfonylbenzoate, N-diaminomethylene-2-methoxy-4-isopropyl-5-methylsulfonylbenzamide;

with methyl 2-methoxy-4-ethyl-5-methylsulfonylbenzoate, N-diaminomethylene-2-methoxy-4-ethyl-5-methylsulfonylbenzamide;

with methyl 2-methoxy-4-butyl-5-methylsulfonylbenzoate, N-diaminomethylene-2-methoxy-4-butyl-5-methylsulfonylbenzamide;

with methyl 2-methoxy-4-(2-butyl)-5-methylsulfonylbenzoate, N-diaminomethylene-2-methoxy-4-(2-butyl)-5-methylsulfonylbenzamide;

with methyl 2-methoxy-4-pentyl-5-methylsulfonylbenzoate, N-diaminomethylene-2-methoxy-4-pentyl-5-methylsulfonylbenzamide;

with methyl 2-methoxy-4-(2-pentyl)-5-methylsulfonylbenzoate, N-diaminomethylene-2-methoxy-4-(2-pentyl)-5-methylsulfonylbenzamide;

with methyl 2-methoxy-4-(3-pentyl)-5-methylsulfonylbenzoate, N-diaminomethylene-2-methoxy-4-(3-pentyl)-5-methylsulfonylbenzamide;

with methyl 2-methoxy-4-hexyl-5-methylsulfonylbenzoate, N-diaminomethylene-2-methoxy-4-hexyl-5-methylsulfonylbenzamide;

with methyl 2-methoxy-4-(2-hexyl)-5-methylsulfonylbenzoate, N-diaminomethylene-2-methoxy-4-(2-hexyl)-5-methylsulfonylbenzamide;

with methyl 2-methoxy-4-(3-hexyl)-5-methylsulfonylbenzoate, N-diaminomethylene-2-methoxy-4-(3-hexyl)-5-methylsulfonylbenzamide;

with methyl 2-methoxy-4-cyclopropyl-5-methylsulfonylbenzoate, N-diaminomethylene-2-methoxy-4-cyclopropyl-5-methylsulfonylbenzamide;

with methyl 2-methoxy-4-cyclopentyl-5-methylsulfonylbenzoate, N-diaminomethylene-2-methoxy-4-cyclopentyl-5-methylsulfonylbenzamide;

with methyl 2-methoxy-4-cyclohexyl-5-methylsulfonylbenzoate, N-diaminomethylene-2-methoxy-4-cyclohexyl-5-methylsulfonylbenzamide;

with methyl 2-methoxy-4-(2-methylcyclopentyl)-5-methylsulfonylbenzoate, N-diaminomethylene-2-methoxy-4-(2-methylcyclopentyl)-5-methylsulfonylbenzamide;

with methyl 2-fluoro-4-methyl-5-methylsulfonylbenzoate, N-diaminomethylene-2-fluoro-4-methyl-5-methylsulfonylbenzamide;

with methyl 2-fluoro-4-ethyl-5-methylsulfonylbenzoate, N-diaminomethylene-2-fluoro-4-ethyl-5-methylsulfonylbenzamide;

with methyl 2-fluoro-4-isopropyl-5-methylsulfonylbenzoate, N-diaminomethylene-2-fluoro-4-isopropyl-5-methylsulfonylbenzamide;

with methyl 2-fluoro-4-propyl-5-methylsulfonylbenzoate, N-diaminomethylene-2-fluoro-4-propyl-5-methylsulfonylbenzamide;

with methyl 2-fluoro-4-butyl-5-methylsulfonylbenzoate, N-diaminomethylene-2-fluoro-4-butyl-5-methylsulfonylbenzamide;

with methyl 2-fluoro-4-(2-butyl)-5-methylsulfonylbenzoate, N-diaminomethylene-2-fluoro-4-(2-butyl)-5-methylsulfonylbenzamide;

with methyl 2-fluoro-4-pentyl-5-methylsulfonylbenzoate, N-diaminomethylene-2-fluoro-4-pentyl-5-methylsulfonylbenzamide;

with methyl 2-fluoro-4-(2-pentyl)-5-methylsulfonylbenzoate, N-diaminomethylene-2-fluoro-4-(2-pentyl)-5-methylsulfonylbenzamide;

with methyl 2-fluoro-4-(3-pentyl)-5-methylsulfonylbenzoate, N-diaminomethylene-2-fluoro-4-(3-pentyl)-5-methylsulfonylbenzamide;

with methyl 2-fluoro-4-hexyl-5-methylsulfonylbenzoate, N-diaminomethylene-2-fluoro-4-hexyl-5-methylsulfonylbenzamide;

with methyl 2-fluoro-4-(2-hexyl)-5-methylsulfonylbenzoate, N-diaminomethylene-2-fluoro-4-(2-hexyl)-5-methylsulfonylbenzamide;

with methyl 2-fluoro-4-(3-hexyl)-5-methylsulfonylbenzoate, N-diaminomethylene-2-fluoro-4-(3-hexyl)-5-methylsulfonylbenzamide;

with methyl 2-fluoro-4-cyclopropyl-5-methylsulfonylbenzoate, N-diaminomethylene-2-fluoro-4-cyclopropyl-5-methylsulfonylbenzamide;

with methyl 2-fluoro-4-cyclopentyl-5-methylsulfonylbenzoate, N-diaminomethylene-2-fluoro-4-cyclopentyl-5-methylsulfonylbenzamide;

with methyl 2-fluoro-4-cyclohexyl-5-methylsulfonylbenzoate, N-diaminomethylene-2-fluoro-4-cyclohexyl-5-methylsulfonylbenzamide;

with methyl 2-fluoro-4-( 2-methylcyclopentyl)-5-methylsulfonylbenzoate, N-diaminomethylene-2-fluoro-4-(2-methylcyclopentyl)-5-mnethylsulfonylbenzamide;

with methyl 2-fluoro-4-(4-methylcyclohexyl)-5-methylsulfonylbenzoate, N-diaminomethylene-2-fluoro-4-(4-methylcyclohexyl)-5-methylsulfonylbenzamide;

with methyl 2-methoxy-4-(4-methylcyclohexyl)-5-methylsulfonylbenzoate, N-diaminomethylene-2-methoxy-4-(4-methylcyclohexyl)-5-methylsulfonylbenzamide.

EXAMPLE 3

100 mg of palladium(II) 1,1'-bis(diphenylphosphine) ferrocene chloride and 100 mg of CuI are added in succession to a suspension of 1 g of N-diaminomethylene-2,3-dimethyl-4-bromo-5-methylsulfonylbenzamide [obtainable by reacting 2,3-dimethyl-4-bromo-5-methylsulfonylbenzoyl chloride with guanidine in the presence of triethylamine] in 100 ml of THF. 10 g of methyl zinc chloride [obtainable from methyl magnesium chloride by transmetalation with $ZnCl_2$ etherate in THF], dissolved in 100 ml of THF, are then added dropwise, and the mixture is stirred at room temperature for 20 h. After filtration, removal of the solvent and customary working up, N-diaminomethylene-2,3,4-trimethyl-5-methylsulfonylbenzamide is obtained, from which the corresponding hydrochloride or methansulfonate is obtained following treatment with a dilute, aqueous solution of HCl or methansulfonic acid and freeze-drying.

EXAMPLE 4

700 mg of N-diaminomethylene-2-bromo-4-methyl-5-methylsulfonylbenzamide [obtainable in accordance with Ex. 2] are suspended in 50 ml of water, and 1.8 ml of 1N HCl are added to this suspension while stirring. Following filtration and lyophilization, N-diaminomethylene-2-bromo-4-methyl-5-methylsulfonylbenzamide; hydrochloride, is obtained, m.p. 232°.

The following hydrochlorides or methansulfonates are obtained from the free bases in an analogous manner:

N-diaminomethylene-2-ethyl-4-methyl-5-methylsulfonylbenzamide, hydrochloride;

N-diaminomethylene-2-propyl-4-methyl-5-methylsulfenylbenzamide, hydrochloride;

N-diaminomethylene-2-isopropyl-4-ethyl-5-methylsulfonylbenzamide, hydrochloride;

N-diaminomethylene-2-butyl-4-methyl-5-methylsulfonylbenzamide, hydrochloride;

N-diaminomethylene-2-(2-butyl)-4-ethylphenyl-5-methylsulfonylbenzamide, hydrochloride;

N-diaminomethylene-2-methyl-4-isopropyl-5-methylsulfonylbenzamide, methansulfonate, m.p. 191°–194°;

N-diaminomethylene-2-propyl-4-isopropyl-5-methylsulfonylbenzamide, hydrochloride;

N-diaminomethylene-2-isopropyl-4-methyl-5-methylsulfonylbenzamide, hydrochloride;

N-diaminomethylene-2-butyl-4-methyl-5-methylsulfonylbenzamide, hydrochloride;

N-diaminomethylene-2-ethyl-4-isopropyl-5-methylsulfonylbenzamide, hydrochloride;

N-diaminomethylene-2,4-diethyl-5-methylsulfonylbenzamide, hydrochloride;

N-diaminomethylene-2-chloro-4-methyl-5-methylsulfonylbenzamide, hydrochloride;

N-diaminomethylene-2-bromo-4-ethyl-5-methylsulfonylbenzamide, hydrochloride;

N-diaminomethylene-2-fluoromethyl-4-methyl-5-methylsulfonylbenzamide, hydrochloride;

N-diaminomethylene-2-trifluoromethyl-4-ethyl-5-methylsulfonylbenzamide, hydrochloride;

N-diaminomethylene-2-pentafluoroethyl-4-methyl-5-methylsulfonylbenzamide, hydrochloride;

N-diaminomethylene-2-methoxy-4-isopropyl-5-methylsulfonylbenzamide, hydrochloride;

N-diaminomethylene-2-cyano-4-methyl-5-mnethylsulfonylbenzamide, hydrochloride;

N-diaminomethylene-2-nitro-4-methyl-5-methylsulfonylbenzamide, hydrochloride;

N-diaminomethylene-2-ethynyl-4-methyl-5-methylsulfonylbenzamide, hydrochloride;

EXAMPLE 5

In analogy with Example 1, N-diaminomethylene-2,4-dimethyl-3-methylsulfonylbenzamide is obtained by reacting 1.2 g of methyl 2,4-dimethyl-3-methylsulfonylbenzoate [obtainable by reacting methyl 2-methyl-3-methylsulfonyl-4-bromobenzoate with methylzinc chloride] with 1.5 g of guanidine in methanol.

The following are obtained in an analogous manner by reacting guanidine.

with methyl 2-methyl-3-methylsulfonyl-4-isopropylbenzoate, N-diaminomethylene-2-methyl-3-methylsulfonyl-4-isopropylbenzamide;

with methyl 2-methyl-3-methylsulfonyl-4-ethylbenzoate, N-diaminomethylene-2-methyl-3-methylsulfonyl-4-ethylbenzamide;

with methyl 2-methyl-3-methylsulfonyl-4-propylbenzoate, N-diaminomethylene-2-methyl-3-methylsulfonyl-4-propylbenzamide;

with methyl 2-methyl-3-methylsulfonyl-4-butylbenzoate, N-diaminomethylene-2-methyl-3-methylsulfonyl-4-butylbenzamide;

with methyl 2-methyl-3-methylsulfonyl-4-(2-butyl)benzoate, N-diaminomethylene-2-methyl-3-methylsulfonyl-4-(2-butyl)benzamide;

with methyl 2-methyl-3-methylsulfonyl-4-pentylbenzoate, N-diaminomethylene-2-methyl-3-methylsulfonyl-4-pentylbenzamide;

with methyl 2-methyl-3-methylsulfonyl-4-(2-pentyl)benzoate, N-diaminomethylene-2-methyl-3-methylsulfonyl-4-(2-pentyl)benzamide;

with methyl 2-methyl-3-methylsulfonyl-4-(3-pentyl)benzoate, N-diaminomethylene-2-methyl-3-methylsulfonyl-4-(3-pentyl)benzamide;

with methyl 2-methyl-3-methylsulfonyl-4-hexylbenzoate, N-diaminomethylene-2-methyl-3-methylsulfonyl-4-hexylbenzanlide;

with methyl 2-methyl-3-methylsulfonyl-4-(2-hexyl)benzoate, N-diaminomethylene-2-methyl-3-methylsulfonyl-4-(2-hexyl)benzamide;

with methyl 2-methyl-3-methylsulfonyl-4-(3-hexyl)benzoate, N-diaminomethylene-2-methyl-3-methylsulfonyl-4-(3-hexyl)benzamide;

with methyl 2-methyl-3-methylsulfonyl-4-cyclopropylbenzoate, N-diaminomethylene-2-methyl-3-methylsulfonyl-4-cyclopropylbenzamide;

with methyl 2-methyl-3-methylsulfonyl-4-cyclopentylbenzoate, N-diaminomethylene-2-methyl-3-methylsulfonyl-4-cyclopentylbenzamide;

with methyl 2-methyl-3-methylsulfonyl-4-cyclohexylbenzoate, N-diaminomethylene-2-methyl-3-methylsulfonyl-4-cyclohexylbenzamide;

with methyl 2-methyl-3-methylsulfonyl-4-(2-methylcyclopentyl)benzoate, N-diaminomethylene-2-methyl-3-methylsulfonyl-4-(2-methylcyclopentyl)benzamide;

with methyl 2-methyl-3-methylsulfonyl-4-(4-methylcyclohexyl)benzoate, N-diaminomethylene-2-methyl-3-methylsulfonyl-4-(4-methylcyclohexyl)benzamide;

with methyl 2-ethyl-3-methylsulfonyl-4-methylbenzoate, N-diaminomethylene-2-ethyl-3-methylsulfonyl-4-methylbenzamide;

with methyl 2-ethyl-3-methylsulfonyl-4-isopropylbenzoate, N-diaminomethylene-2-ethyl-3-methylsulfonyl-4-isopropylbenzamide;

with methyl 2-ethyl-3-methylsulfonyl-4-propylbenzoate, N-diaminomethylene-2-ethyl-3-methylsulfonyl-4-propylbenzamide;

with methyl 2-ethyl-3-methylsulfonyl-4-butylbenzoate, N-diaminomethylene-2-ethyl-3-methylsulfonyl-4-butylbenzamide;

with methyl 2-ethyl-3-methylsulfonyl-4-(2-butyl)benzoate, N-diaminomethylene-2-ethyl-3-methylsulfonyl-4-(2-butyl)benzamide;

with methyl 2-ethyl-3-methylsulfonyl-4-pentylbenzoate, N-diaminomethylene-2-ethyl-3-methylsulfonyl-4-pentylbenzamide;

with methyl 2-ethyl-3-methylsulfonyl-4-(2-pentyl)benzoate, N-diaminomethylene-2-ethyl-3-methylsulfonyl-4-(2-pentyl)benzamide;

with methyl 2-ethyl-3-methylsulfonyl-4-(3-pentyl)benzoate, N-diaminomethylene-2-ethyl-3-methylsulfonyl-4-(3-pentyl)benzamide;

with methyl 2-ethyl-3-methylsulfonyl-4-hexylbenzoate, N-diaminomethylene-2-ethyl-3-methylsulfonyl-4-hexylbenzamide;

with methyl 2-ethyl-3-methylsulfonyl-4-(2-hexyl)benzoate, N-diaminomethylene-2-ethyl-3-methylsulfonyl-4-(2-hexyl)benzamide;

with methyl 2-ethyl-3-methylsulfonyl-4-(3-hexyl)benzoate, N-diaminomethylene-2-ethyl-3-methylsulfonyl-4-(3-hexyl)benzamide;

with methyl 2-ethyl-3-methylsulfonyl-4-cyclopropylbenzoate, N-diaminomethylene-2-ethyl-3-methylsulfonyl-4-cyclopropylbenzamide;

with methyl 2-ethyl-3-methylsulfonyl-4-cyclopentylbenzoate, N-diaminomethylene-2-ethyl-3-methylsulfonyl-4-cyclopentylbenzamide;

with methyl 2-ethyl-3-methylsulfonyl-4-cyclohexylbenzoate, N-diaminomethylene-2-ethyl-3-methylsulfonyl-4-cyclohexylbenzamide;

with methyl 2-ethyl-3-methylsulfonyl-4-(2-methylcyclopentyl)benzoate, N-diaminomethylene-2-ethyl-3-methylsulfonyl-4-(2-methylcyclopentyl)benzamide;

with methyl 2-ethyl-3-methylsulfonyl-4-(4-methylcyclohexyl)benzoate, N-diaminomethylene-2-ethyl-3-methylsulfonyl-4-(4-methylcyclohexyl)benzamide;

with methyl 2-propyl-3-methylsulfonyl-4-methylbenzoate, N-diaminomethylene-2-propyl-3-methylsulfonyl-4-methylbenzamide;

with methyl 2-propyl-3-methylsulfonyl-4-isopropylbenzoate, N-diaminomethylene-2-propyl-3-methylsulfonyl-4-isopropylbenzamide;

with methyl 2-propyl-3-methylsulfonyl-4-ethylbenzoate, N-diaminomethylene-2-propyl-3-methylsulfonyl-4-ethylbenzamide;

with methyl 2-propyl-3-methylsulfonyl-4-butylbenzoate, N-diaminomethylene-2-propyl-3-methylsulfonyl-4-butylbenzamide;

with methyl 2-propyl-3-methylsulfonyl-4-(2-butyl)benzoate, N-diaminomethylene-2-propyl-3-methylsulfonyl-4-(2-butyl)benzamide;

with methyl 2-propyl-3-methylsulfonyl-4-pentylbenzoate, N-diaminomethylene-2-propyl-3-methylsulfonyl-4-pentylbenzamide;

with methyl 2-propyl-3-methylsulfonyl-4-(2-pentyl) benzoate, N-diaminomethylene-2-propyl-3-methylsulfonyl-4-(2-pentyl)benzamide;
with methyl 2-propyl-3-methylsulfonyl-4-(3-pentyl) benzoate, N-diaminomethylene-2-propyl-3-methylsulfonyl-4-(3-pentyl)benzamide;
with methyl 2-propyl-3-methylsulfonyl-4-hexylbenzoate, N-diaminomethylene-2-propyl-3-methylsulfonyl-4-hexylbenzamide;
with methyl 2-propyl-3-methylsulfonyl-4-(2-hexyl) benzoate, N-diaminomethylene-2-propyl-3-methylsulfonyl-4-(2-hexyl)benzamide;
with methyl 2-propyl-3-methylsulfonyl-4-(3-hexyl) benzoate, N-diaminomethylene-2-propyl-3-methylsulfonyl-4-(3-hexyl)benzamide;
with methyl 2-propyl-3-methylsulfonyl-4-cyclopropylbenzoate, N-diaminomethylene-2-propyl-3-methylsulfonyl-4-cyclopropylbenzamide;
with methyl 2-propyl-3-methylsulfonyl-4-cyclopentylbenzoate, N-diaminomethylene-2-propyl-3-methylsulfonyl-4-cyclopentylbenzamide;
with methyl 2-propyl-3-methylsulfonyl-4-cyclohexylbenzoate, N-diaminomethylene-2-propyl-3-methylsulfonyl-4-cyclohexylbenzamide;
with methyl 2-propyl-3-methylsulfonyl-4-(2-methylcyclopentyl)benzoate, N-diaminomethylene-2-propyl-3-methylsulfonyl-4-(2-methylcyclopentyl)benzamide;
with methyl 2-propyl-3-methylsulfonyl-4-(4-methylcyclohexyl)benzoate, N-diaminomethylene-2-propyl-3-methylsulfonyl-4-(4-methylcyclohexyl)benzamide;
with methyl 2-fluoromethyl-3-methylsulfonyl-4-methylbenzoate, N-diaminomethylene-2-fluoromethyl-3-methylsulfonyl-4-dimethylbenzamide;
with methyl 2-difluoromethyl-3-methylsulfonyl-4-ethylbenzoate, N-diaminomethylene-2-difluoromethyl-3-methylsulfonyl-4-ethylbenzamide;
with methyl 2-bromo-3-methylsulfonyl-4-propylbenzoate, N-diaminomethylene-2-bromo-3-methylsulfonyl-4-propylbenzamide;
with methyl 2-chloro-3-methylsulfonyl-4-butylbenzoate, N-diaminomethylene-2-chloro-3-methylsulfonyl-4-butylbenzamide;
with methyl 2-bromo-3-methylsulfonyl-4-(2-butyl) benzoate, N-diaminomethylene-2-bromo-3-methylsulfonyl-4-(2-butyl)benzamide;
with methyl 2-trifluoromethyl-3-methylsulfonyl-4-pentylbenzoate, N-diaminomethylene-2-trifluoromethyl-3-methylsulfonyl-4-pentylbenzamide;
with methyl 2-fluoromethyl-3-methylsulfonyl-4-(2-pentyl) benzoate, N-diaminomethylene-2-fluoromethyl-3-methylsulfonyl-4-(2-pentyl)benzamide;
with methyl 2-bromo-3-methylsulfonyl-4-(3-pentyl) benzoate, N-diaminomethylene-2-bromo-3-methylsulfonyl-4-(3-pentyl)benzamide;
with methyl 2-chloro-3-methylsulfonyl-4-hexylbenzoate, N-diaminomethylene-2-chloro-3-methylsulfonyl-4-hexylbenzamide;
with methyl 2-difluoromethyl-3-methylsulfonyl-4-(2-hexyl) benzoate, N-diaminomethylene-2-difluoromethyl-3-methylsulfonyl-4-(2-hexyl)benzamide;
with methyl 2-bromo-3-methylsulfonyl-4-(3-hexyl) benzoate, N-diaminomethylene-2-bromo-3-methylsulfonyl-4-(3-hexyl)benzamide;
with methyl 2-bromo-3-methylsulfonyl-4-cyclopropylbenzoate, N-diaminomethylene-2-bromo-3-methylsulfonyl-4-cyclopropylbenzamide;
with methyl 2-bromo-3-methylsulfonyl-4-cyclopentylbenzoate, N-diaminomethylene-2-bromo-3-methylsulfonyl-4-cyclopentylbenzamide;
with methyl 2-bromo-3-methylsulfonyl-4-cyclohexylbenzoate, N-diaminomethylene-2-bromo-3-methylsulfonyl-4-cyclohexylbenzamide;
with methyl 2-bromo-3-methylsulfonyl-4-(2-methylcyclopentyl)benzoate, N-diaminomethylene-2-bromo-3-methylsulfonyl-4-(2-methylcyclopentyl)benzamide;
with methyl 2-bromo-3-methylsulfonyl-4-(4-methylcyclohexyl)benzoate, N-diaminomethylene-2-bromo-3-methylsulfonyl-4-(4-methylcyclohexyl)benzamide;
with methyl 2-cyano-3-methylsulfonyl-4-ethylbenzoate, N-diaminomethylene-2-cyano-3-methylsulfonyl-4-ethylbenzamide;
with methyl 2-cyano-3-methylsulfonyl-4-methylbenzoate, N-diaminomethylene-2-cyano-3-methylsulfonyl-4-methylbenzamide;
with methyl 2-cyano-3-methylsulfonyl-4-isopropylbenzoate, N-diaminomethylene-2-cyano-3-methylsulfonyl-4-isopropylbenzamide;
with methyl 2-cyano-3-methylsulfonyl-4-propylbenzoate, N-diaminomethylene-2-cyano-3-methylsulfonyl-4-propylbenzamide;
with methyl 2-nitro-3-methylsulfonyl-4-butylbenzoate, N-diaminomethylene-2-nitro-3-methylsulfonyl-4-butylbenzamide;
with methyl 2-ethynyl-3-methylsulfonyl-4-(2-butyl) benzoate, N-diaminomethylene-2-ethynyl-3-methylsulfonyl-4-(2-butyl)benzamide;
with methyl 2-ethynyl-3-methylsulfonyl-4-pentylbenzoate, N-diaminomethylene-2-ethynyl-3-methylsulfonyl-4-pentylbenzamide;
with methyl 2-cyano-3-methylsulfonyl-4-(2-pentyl) benzoate, N-diaminomethylene-2-cyano-3-methylsulfonyl-4-(2-pentyl)benzamide;
with methyl 2-fluoro-3-methylsulfonyl-4-methylbenzoate, N-diaminomethylene-2-fluoro-3-methylsulfonyl-4-methylbenzamide;
with methyl 2-fluoro-3-methylsulfonyl-4-ethylbenzoate, N-diaminomethylene-2-fluoro-3-methylsulfonyl-4-ethylbenzamide;
with methyl 2-fluoro-3-methylsulfonyl-4-isopropylbenzoate, N-diaminomethylene-2-fluoro-3-methylsulfonyl-4-isopropylbenzamide;
with methyl 2-fluoro-3-methylsulfonyl-4-propylbenzoate, N-diaminomethylene-2-fluoro-3-methylsulfonyl-4-propylbenzamide;
with methyl 2-fluoro-3-methylsulfonyl-4-butylbenzoate, N-diaminomethylene-2-fluoro-3-methylsulfonyl-4-butylbenzamide;
with methyl 2-fluoro-3-methylsulfonyl-4-(2-butyl)benzoate, N-diaminomethylene-2-fluoro-3-methylsulfonyl-4-(2-butyl)benzamide;
with methyl 2-fluoro-3-methylsulfonyl-4-pentylbenzoate, N-diaminomethylene-2-fluoro-3-methylsulfonyl-4-pentylbenzamide;
with methyl 2-fluoro-3-methylsulfonyl-4-(2-pentyl) benzoate, N-diaminomethylene-2-fluoro-3-methylsulfonyl-4-(2-pentyl)benzamide;
with methyl 2-fluoro-3-methylsulfonyl-4-(3-pentyl) benzoate, N-diaminomethylene-2-fluoro-3-methylsulfonyl-4-(3-pentyl)benzamide;
with methyl 2-fluoro-3-methylsulfonyl-4-hexylbenzoate, N-diaminomethylene-2-fluoro-3-methylsulfonyl-4-hexylbenzamide;

with methyl 2-fluoro-3-methylsulfonyl-4-(2-hexyl) benzoate, N-diaminomethylene-2-fluoro-3-methylsulfonyl-4-(2-hexyl)benzamide;

with methyl 2-fluoro-3-methylsulfonyl-4-(3-hexyl) benzoate, N-diaminomethylene-2-fluoro-3-methylsulfonyl-4-(3-hexyl)benzamide;

with methyl 2-fluoro-3-methylsulfonyl-4-cyclopropylbenzoate, N-diaminomethylene-2-fluoro-3-methylsulfonyl-4-cyclopropylbenzamide;

with methyl 2-fluoro-3-methylsulfonyl-4-cyclopentylbenzoate, N-diaminomethylene-2-fluoro-3-methylsulfonyl-4-cyclopentylbenzamide;

with methyl 2-fluoro-3-methylsulfonyl-4-cyclohexylbenzoate, N-diaminomethylene-2-fluoro-3-methylsulfonyl-4-cyclohexylbenzamide;

with methyl 2-fluoro-3-methylsulfonyl-4-(2-methylcyclopentyl)benzoate, N-diaminomethylene-2-fluoro-3-methylsulfonyl-4-(2-methylcyclopentyl) benzamide;

with methyl 2-fluoro-3-methylsulfonyl-4-(4-methylcyclohexyl)benzoate, N-diaminomethylene-2-fluoro-3-methylsulfonyl-4-(4-methylcyclohexyl) benzamide;

with methyl 2-nitro-3-methylsulfonyl-4-(3-pentyl)benzoate, N-diaminomethylene-2-nitro-3-methylsulfonyl-4-(3-pentyl)benzamide;

with methyl 2-ethynyl-3-methylsulfonyl-4-hexylbenzoate, N-diaminomethylene-2-ethynyl-3-methylsulfonyl-4-hexylbenzamide;

with methyl2-cyano-3-methylsulfonyl-4-(2-hexyl)benzoate, N-diaminomethylene-2-cyano-3-methylsulfonyl-4-(2-hexyl)benzamide;

with methyl 2-pentafluoroethyl-3-methylsulfonyl-4-(3-hexyl)benzoate, N-diaminomethylene-2-pentafluoroethyl-3-methylsulfonyl-4-(3-hexyl)benzamide;

with methyl 2-cyano-3-methylsulfonyl-4-cyclopropylbenzoate, N-diaminomethylene-2-cyano-3-methylsulfonyl-4-cyclopropylbenzamide;

with methyl 2-ethynyl-3-methylsulfonyl-4-cyclopentylbenzoate, N-diaminomethylene-2-ethynyl-3-methylsulfonyl-4-cyclopentylbenzamide;

with methyl 2-cyano-3-methylsulfonyl-4-cyclohexylbenzoate, N-diaminomethylene-2-cyano-3-methylsulfonyl-4-cyclohexylbenzamide;

with methyl 2-nitro-3-methylsulfonyl-4-(2-methylcyclopentyl)benzoate, N-diaminomethylene-2-nitro-3-methylsulfonyl-4-(2-methylcyclopentyl)benzamide;

with methyl 2-pentafluoroethyl-3-methylsulfonyl-4-(4-methylcyclohexyl)benzoate, N-diaminomethylene-2-pentafluoroethyl-3-methylsulfonyl-4-(4-methylcyclohexyl)benzamide;

with methyl 2-pentafluoroethyl-3-methylsulfonyl-4-propylbenzoate, N-diaminomethylene-2-pentafluoroethyl-3-methylsulfonyl-4-propylbenzamide;

with methyl 2-methoxy-3-methylsulfonyl-4-methylbenzoate, N-diaminomethylene-2-methoxy-3-methylsulfonyl-4-methylbenzamide;

with methyl 2-methoxy-3-methylsulfonyl-4-isopropylbenzoate, N-diaminomethylene-2-methoxy-3-methylsulfonyl-4-isopropylbenzamide;

with methyl 2-methoxy-3-methylsulfonyl-4-ethylbenzoate, N-diaminomethylene-2-methoxy-3-methylsulfonyl-4-ethylbenzamide;

with methyl 2-methoxy-3-methylsulfonyl-4-butylbenzoate, N-diaminomethylene-2-methoxy-3-methylsulfonyl-4-butylbenzamide;

with methyl 2-methoxy-3-methylsulfonyl-4-(2-butyl)benzoate, N-diaminomethylene-2-methoxy-3-methylsulfonyl-4-(2-butyl)benzamide;

with methyl 2-methoxy-3-methylsulfonyl-4-pentylbenzoate, N-diaminomethylene-2-methoxy-3-methylsulfonyl-4-pentylbenzamide;

with methyl 2-methoxy-3-methylsulfonyl-4-(2-pentyl)benzoate, N-diaminomethylene-2-methoxy-3-methylsulfonyl-4-(2-pentyl)benzamide;

with methyl 2-methoxy-3-methylsulfonyl-diamino-3-pentyl)benzoate, N-diaminomethylene-2-methoxy-3-methylsulfonyl-4-(3-pentyl)benzamide;

with methyl 2-methoxy-3-methylsulfonyl-4-hexylbenzoate, N-diaminomethylene-2-methoxy-3-methylsulfonyl-4-hexylbenzamide;

with methyl 2-methoxy-3-methylsulfonyl-4-(2-hexyl) benzoate, N-diaminomethylene-2-methoxy-3-methylsulfonyl-4-(2-hexyl)benzamide;

with methyl 2-methoxy-3-methylsulfonyl-4-(3-hexyl) benzoate, N-diaminomethylene-2-methoxy-3-methylsulfonyl-4-(3-hexyl)benzamide;

with methyl 2-methoxy-3-methylsulfonyl-4-cyclopropylbenzoate, N-diaminomethylene-2-methoxy-3-methylsulfonyl-4-cyclopropylbenzamide;

with methyl 2-methoxy-3-methylsulfonyl-4-cyclopentylbenzoate, N-diaminomethylene-2-methoxy-3-methylsulfonyl-4-cyclopentylbenzamide;

with methyl 2-methoxy-3-methylsulfonyl-4-cyclohexylbenzoate, N-diaminomethylene-2-methoxy-3-methylsulfonyl-4-cyclohexylbenzamide;

with methyl 2-methoxy-3-methylsulfonyl-4-(2-methylcyclopentyl)benzoate, N-diaminomethylene-2-methoxy-3-methylsulfonyl-4-(2-methylcyclopentyl) benzamide;

with methyl 2-methoxy-3-methylsulfonyl-4-(4-methylcyclohexyl)benzoate, N-diaminomethylene-2-methoxy-3-methylsulfonyl-4-(4-methylcyclohexyl) benzamide.

EXAMPLE 6

100 mg of Pd(II) 1,1'-bis(diphenylphosphine)ferrocene chloride, 100 mg of CuI and 10 equivalents of cyclopentylzinc chloride, dissolved in 100 ml of THF, are added in succession to a suspension of 1 g of N-diaminomethylene-2-methoxy-3-methyl-4-bromo-5-methylsulfonylbezamine [obtainable by reacting 2-methoxy-3-methyl-4-bromo-5-methylsulfonylbenzoyl chloride with guanidine in the presence of triethylamine] in 70 ml of THF, and the mixture is stirred at room temperature for 20 hours. Following filtration, removal of the solvent and customary working-up, N-diaminomethylene-2-methoxy-3-methyl-4-cyclopentyl-5-methylsulfonylbenzamide is then obtained, from which the corresponding hydrochloride is obtained after treatment with a dilute, aqueous solution of HCl and freeze-drying.

EXAMPLE 7

In analogy with Example 1, N-diaminomethylene-2-ethyl-3-aminosulfonyl-4-methylbenzamide is obtained by reacting 1.0 g of methyl 2-ethyl-3-aminosulfonyl-4-methylbenzoate [obtainable by reacting methyl 2-ethyl-3-aminosulfonyl-4-bromobenzoate with methylzinc chloride in the presence of bis(triphenylphosphine)palladium(II) chloride] with 0.9 g of guanidinium chloride.

The following are obtained in an analogous manner from methyl 2-methyl-3-aminosulfonyl-4-isopropylbenzoate, N-diaminomethylene-2-methyl-3-aminosulfonyl-4-isopropylbenzamide;

from methyl 2-ethyl-3-aminosulfonyl-4-methylbenzoate, N-diaminomethylene-2-ethyl-3-aminosulfonyl-4-methylbenzamide;

from methyl 2-cyano-3-aminosulfonyl-4-methylbenzoate, N-diaminomethylene-2-cyano-3-aminosulfonyl-4-methylbenzamide;

from methyl 2-ethyl-3-aminosulfonyl-4-propylbenzoate, N-diaminomethylene-2-ethyl-3-aminosulfonyl-4-propylbenzamide;

from methyl 2-bromo-3-aminosulfonyl-4-ethylbenzoate, N-diaminomethylene-2-bromo-3-aminosulfonyl-4-ethylbenzamide;

from methyl 2-difluoromethyl-3-aminosulfonyl-4-methylbenzoate, N-diaminomethylene-2-difluoromethyl-3-aminosulfonyl-4-ethylbenzamide;

from methyl 2-fluoromethyl-3-aminosulfonyl-4-methylbenzoate, N-diaminomethylene-2-fluoromethyl-3-aminosulfonyl-4-methylbenzamide.

EXAMPLE 8

In analogy with Example 1, N-diaminomethylene-2-methyl-4-ethyl-5-aminosulfonylbenzamide is obtained by reacting 1.8 g of methyl 2-methyl-4-ethyl-5-aminosulfonylbenzoate [obtainable by reacting methyl 3-aminosulfonyl-4-bromo-6-methylbenzoate with ethylzinc chloride] with 1.5 g of guanidine in methanol.

The following are obtained in an analogous manner by reacting guanidine with methyl 2-ethyl-4-isopropyl-5-aminosulfonylbenzoate, N-diaminomethylene-2-ethyl-4-isopropyl-5-aminosulfonylbenzamide;

with methyl 2-propyl-4-methyl-5-aminosulfonylbenzoate, N-diaminomethylene-2-propyl-4-methyl-5-aminosulfonylbenzamide;

with methyl 2-isopropyl-4-methyl-5-aminosulfonylbenzoate, N-diaminomethylene-2-isopropyl-4-methyl-5-aminosulfonylbenzamide;

with methyl 2-butyl-4-methyl-5-aminosulfonylbenzoate, N-diaminomethylene-2-butyl-4-methyl-5-aminosulfonylbenzamide;

with methyl 2-but-2-yl-4-methyl-5-aminosulfonylbenzoate, N-diaminomethylene-2-but-2-yl-4-methyl-5-aminosulfonylbenzamide;

with methyl 2-ethyl-4-propyl-5-aminosulfonylbenzoate, N-diaminomethylene-2-ethyl-4-propyl-5-aminosulfonylbenzamide;

with methyl 2-propyl-4-ethyl-5-aminosulfonylbenzoate, N-diaminomethylene-2-propyl-4-ethyl-5-aminosulfonylbenzamide;

with methyl 2-isopropyl-4-ethyl-5-aminosulfonylbenzoate, N-diaminomethylene-2-isopropyl-4-ethyl-5-aminosulfonylbenzamide;

with methyl 2-butyl-4-ethyl-5-aminosulfonylbenzoate, N-diaminomethylene-2-butyl-4-ethyl-5-aminosulfonylbenzamide;

with methyl 2—(2-butyl)-4-ethyl-5-aminosulfonylbenzoate, N-diaminomethylene-2-but-2-yl-4-ethyl-5-aminosulfonylbenzamide;

with methyl 2-ethyl-4-methyl-5-aminosulfonylbenzoate, N-diaminomethylene-2-ethyl-4-methyl-5-aminosulfonylbenzamide;

with methyl 2-chloro-4-methyl-5-aminosulfonylbenzoate, N-diaminomethylene-2-chloro-4-methyl-5-aminosulfonylbenzamide;

with methyl 2-bromo-4-methyl-5-aminosulfonylbenzoate, N-diaminomethylene-2-bromo-4-methyl-5-aminosulfonylbenzamide;

with methyl 2-fluoromethyl-4-methyl-5-aminosulfonylbenzoate, N-diaminomethylene-2-fluoromethyl-4-methyl-5-aminosulfonylbenzamide;

with methyl 2-trifluoromethyl-4-methyl-5-aminosulfonylbenzoate, N-diaminomethylene-2-trifluoromethyl-4-methyl-5-aminosulfonylbenzamide;

with methyl 2-pentafluoroethyl-4-methyl-5-aminosulfonylbenzoate, N-diaminomethylene-2-pentafluoroethyl-4-methyl-5-aminosulfonylbenzamide;

with methyl 2-methoxy-4-methyl-5-aminosulfonylbenzoate, N-diaminomethylene-2-methoxy-4-methyl-5-aminosulfonylbenzamide;

with methyl 2-cyano-4-methyl-5-aminosulfonylbenzoate, N-diaminomethylene-2-cyano-4-methyl-5-aminosulfonylbenzamide;

with methyl 2-nitro-4-methyl-5-aminosulfonylbenzoate, N-diaminomethylene-2-nitro-4-methyl-5-aminosulfonylbenzamide;

with methyl 2-ethynyl-4-methyl-5-aminosulfonylbenzoate, N-diaminomethylene-2-ethynyl-4-methyl-5-aminosulfonylbenzamide.

The examples given below relate to pharmaceutical preparations.

EXAMPLE A

Injection vials

A solution of 100 g of an active compound of the formula I and 5 g of disodium hydrogen phosphate in 3 l of double-distilled water is adjusted to pH 6.5 using 2N hydrochloric acid, sterilized by filtration and used to fill injection vials; the solution in the vials is then lyophilized under sterile conditions and the vials are then sealed in a sterile manner. Each injection vial contains 5 mg of active compound.

EXAMPLE B

Suppositories

A mixture of 20 g of an active compound of the formula I is melted together with 100 g of soyabean lecithin and 1400 g of cocoa butter and the mixture is poured into molds and allowed to cool. Each suppository contains 20 mg of active compound.

EXAMPLE C

Solution

A solution is prepared consisting of 1 g of an active compound of the formula I, 9.38 g of $NaH_2PO_4.2\ H_2O$, 28.48 g of $Na_2HPO_4.12\ H_2O$ and 0.1 g of benzalkonium chloride in 940 ml of double-distilled water. The solution is adjusted to pH 6.8, made up to 1 l and sterilized by irradiation. This solution can be used in the form of eye drops, for example.

EXAMPLE D

Ointment 500 mg of an active compound of the formula I is mixed with 99.5 g of vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed, in a customary manner, into tablets such that each tablet contains 10 mg of active compound.

EXAMPLE F

Coated tablets

Tablets are compressed in analogy with Example E, which tablets are subsequently coated, in a customary manner, with a coating consisting of sucrose, potato starch, talc, gum tragacanth and coloring matter.

EXAMPLE G

Capsules

Hard gelatine capsules are filled, in a customary manner, with 2 kg of active compound of the formula I such that each capsule contains 20 mg of the active compound.

EXAMPLE H

Ampoules

A solution of 1 kg of active compound of the formula I in 60 l of double-distilled water is sterilized by filtration and used to fill ampoules; the solution in the ampoules is lyophilized under sterile conditions and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An alkylbenzoylguanidine of the formula I

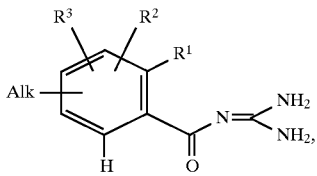

in which $R^1$ is A, $CF_3$, $CH_2F$, $CHF_2$, $C_2F_5$, CN, $NO_2$, Hal, C≡CH or —X—$R^4$, $R^2$ and $R^3$ are in each case, independently of each other, H, Hal, A, —X—$R^4$, CN, $NO_2$, $CF_3$, $CH_2F$, $CHF_2$, $C_2F_5$, $CH_2CF_3$, —$SO_n$—$R^{hu\ 6}$, —$SO_2NR^4R^5$, Ph or OPh, $R^4$ is H, A, cycloalkyl having from 5 to 7 C atoms, cycloalkylmethyl having from 6 to 8 C atoms, $CF_3$, $CH_2F$, $CHF_2$, $CH_2CF_3$, Ph or —$CH_2$—Ph, $R^5$ is H or A, $R^6$ is A or Ph, Alk is located in the para-position on the ring with respect to the guanidine group and is a straight-chain or branched $C_1$–$C_8$-alkyl radical, $C_3$–$C_8$-cycloalkyl which can be unsubstituted or substituted once, twice or three times by A, or is —$CR^7$=$CHR^{7'}$ or —C≡$CR^7$, $R^7$ and $R^{7'}$ are in each case, independently of each other, H, A or Ph, A is alkyl having from 1 to 6 C atoms, Hal is F, Cl, Br or I, X is O, S or $NR^5$, Ph is phenyl which is unsubstituted or substituted once, twice or three times by A, OA, $NR^4R^5$, F, Cl, Br, I or $CF_3$, and n is 1 or 2, and the physiologically tolerable salts thereof.

2. A compound:
   (a) Diaminomethylene-2-methyl-4-isopropyl-5-methylsulfonylbenzamide;
   (b) N-Diaminomethylene-2,4-dimethyl-5-methylsulfonylbenzamide;
   (c) N-Diaminomethylene-2-bromo-4-methyl-5-methylsulfonylbenzamide;
   (d) N-Diaminomethylene-2-ethyl-4-isopropyl-5-methylsulfonylbenzamide;
   (e) N-Diaminomethylene-2-ethyl-4-cyclopentyl-5-methylsulfonylbenzamide;
   (f) N-Diaminomethylene-2-methyl-3-methylsulfonyl-4-cyclopentylbenzamide;
   (g) N-Diaminomethylene-2-ethyl-3-methylsulfonyl-4-cyclopentylbenzamide;

according to claim 1, and the physiologically tolerable salts thereof.

3. A process for preparing an alkylbenzoylguanidine of the formula I according to claim 1, and also their salts, comprising reacting a compound of the formula II

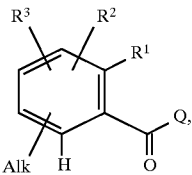

in which $R^1$, $R^2$, $R^3$ and Alk have the previously mentioned meanings, and Q is Cl, Br, OA, O—CO—A, O—CO—Ph, OH, or another reactive esterified OH group or a leaving group which can readily be substituted nucleophilically, with guanidine, or reacting a benzoylguanidine of the formula III

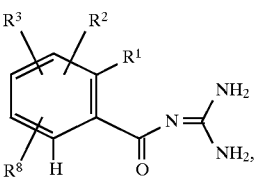

in which $R^1$, $R^2$, $R^3$ and Alk have the previously mentioned meanings, and $R^8$ is F, Cl, Br, I or H, with a compound of the formula IV

in which

Alk has the given meaning, and $R^{8'}$ is H, Cl, Br or I, in the presence of a catalyst and following prior metalation or transmetalation, or treating a compound which contains one or more reducible group(s) and/or one or more additional C—C and/or C—N bond(s) in place of one or more hydrogen atoms, but which otherwise conforms to the formula I, with a reducing agent, or treating a compound which contains one or more solvolyzable group(s) in a place of one or more hydrogen atoms, but which otherwise conforms to the formula I, with a solvolyzing agent, and/or converting a base of the formula I which has been obtained into one of its salts by treatment with an acid.

4. A process for producing pharmaceutical preparations, wherein a compound of the formula I according to claim 1 and/or one of its physiologically harmless salts is/are brought together with at least one solid, liquid or semi-liquid carrier substance or auxiliary substance, into a suitable dosage form.

5. A pharmaceutical preparation, comprising at least one compound of the formula I according to claim 1 and/or one of its physiologically tolerable salts and suitable auxiliaries.

6. A method for treating or preventing arrhythmias, angina pectoris and infarctions which comprises administering to a patient in need thereof an effective amount of a compound of the formula I of claim 1.

7. An alkylbenzoylguanidine of claim 1, wherein $R^1$ is A and $R^2$ is —$SO_2$—A or —$SO_2$—$NH_2$.

8. An alkylbenzoylguanidine of claim 1, wherein $R^1$ is A or Hal, and Alk is a branched or unbranched alkyl group having 1 to 8 C atoms.

9. An alkylbenzoylguanidine of claim 1, wherein $R^1$ is A or Hal, and Alk is a cycloalkyl group having 3 to 8 C atoms.

10. An alkylbenzoylguanidine of claim 1, wherein $R^2$ is —$SO_2$—A or —$SO_2$—$NH_2$, and $R^1$ is A, OA or Hal.

11. An alkylbenzoylguanidine of claim 1, wherein the Alk group is methyl, ethyl, propyl or isopropyl, and $R^2$ is —$SO_2$—A or —$SO_2$—$NH_2$, and is located in the meta position with respect to the guanidine group.

12. An alkylbenzoylguanidine of claim 1, wherein $R^1$ and $R^2$ are at adjacent positions on the ring and $R^1$ is A, OA or Hal, and $R^2$ is —$SO_2$—A.

13. An alkylbenzoylguanidine of claim 1, wherein the Alk group is cyclopropyl, cyclopentyl or cyclohexyl, and $R^2$ is located in the meta position with respect to the guanidine and is —$SO_2$—A.

14. An alkylbenzoylguanidine of claim 1, wherein $R^1$ is A, OA or Hal, $R^2$ is —$SO_2$—A and the Alk group is methyl, ethyl, propyl, isopropyl, cyclopentyl or cyclohexyl.

15. A method for treating or controlling a disease treatable by inhibition of the cellular $Na^+/H^+$ antiporter which comprises administering a cellular $Na^+/H^+$ antiporter inhibiting effective amount of an alkylbenzoylguanidine of claim 1 to a human or animal in need thereof.

16. The method of claim 15, wherein the alkylbenzoylguanidine is administered in a daily dose of 0.0001–0.1 mg/kg of body weight.

17. The method of claim 6, wherein the compound of formula I is administered in a daily dose of 0.0001–0.1 mg/kg of body weight.

* * * * *